(12) United States Patent
Verona

(10) Patent No.: US 6,270,752 B1
(45) Date of Patent: Aug. 7, 2001

(54) COSMETIC FORMULATIONS FOR THE PREVENTION AND THERAPY OF HAIR LOSS

(76) Inventor: Giancarlo Verona, Via Mascheroni, 12 - Milano (IT)

( * ) Notice: Subject to any disclaimer, the term of this patent is extended or adjusted under 35 U.S.C. 154(b) by 0 days.

(21) Appl. No.: 09/529,544

(22) PCT Filed: Apr. 17, 1998

(86) PCT No.: PCT/EP98/02253

§ 371 Date: Apr. 14, 2000

§ 102(e) Date: Apr. 14, 2000

(87) PCT Pub. No.: WO99/20232

PCT Pub. Date: Apr. 29, 1999

(30) Foreign Application Priority Data

Oct. 17, 1997 (IT) ............................................. MI97A02353

(51) Int. Cl.$^7$ ....................................................... A61K 7/06
(52) U.S. Cl. ........................... 424/70.1; 424/401; 514/880
(58) Field of Search .................................. 424/401, 70.1; 514/880

(56) References Cited

FOREIGN PATENT DOCUMENTS

| 2 378 512 | 8/1978 | (FR). |
| WO 91/06278 | 4/1991 | (WO). |
| WO 94/07454 | 4/1994 | (WO). |

*Primary Examiner*—Shelley A. Dodson
*Assistant Examiner*—Konata M. George
(74) *Attorney, Agent, or Firm*—Young & Thompson

(57) ABSTRACT

Formulations for the prevention and therapy of hair loss and seborrhoea are based on essential oils obtainable through alcoholic distillation of plants which contain the essential oils, combined with salicylic acid and with fatty acids having 10 to 40 carbon atoms.

15 Claims, 1 Drawing Sheet

COSMETIC FORMULATIONS FOR THE PREVENTION AND THERAPY OF HAIR LOSS

Figure 1:
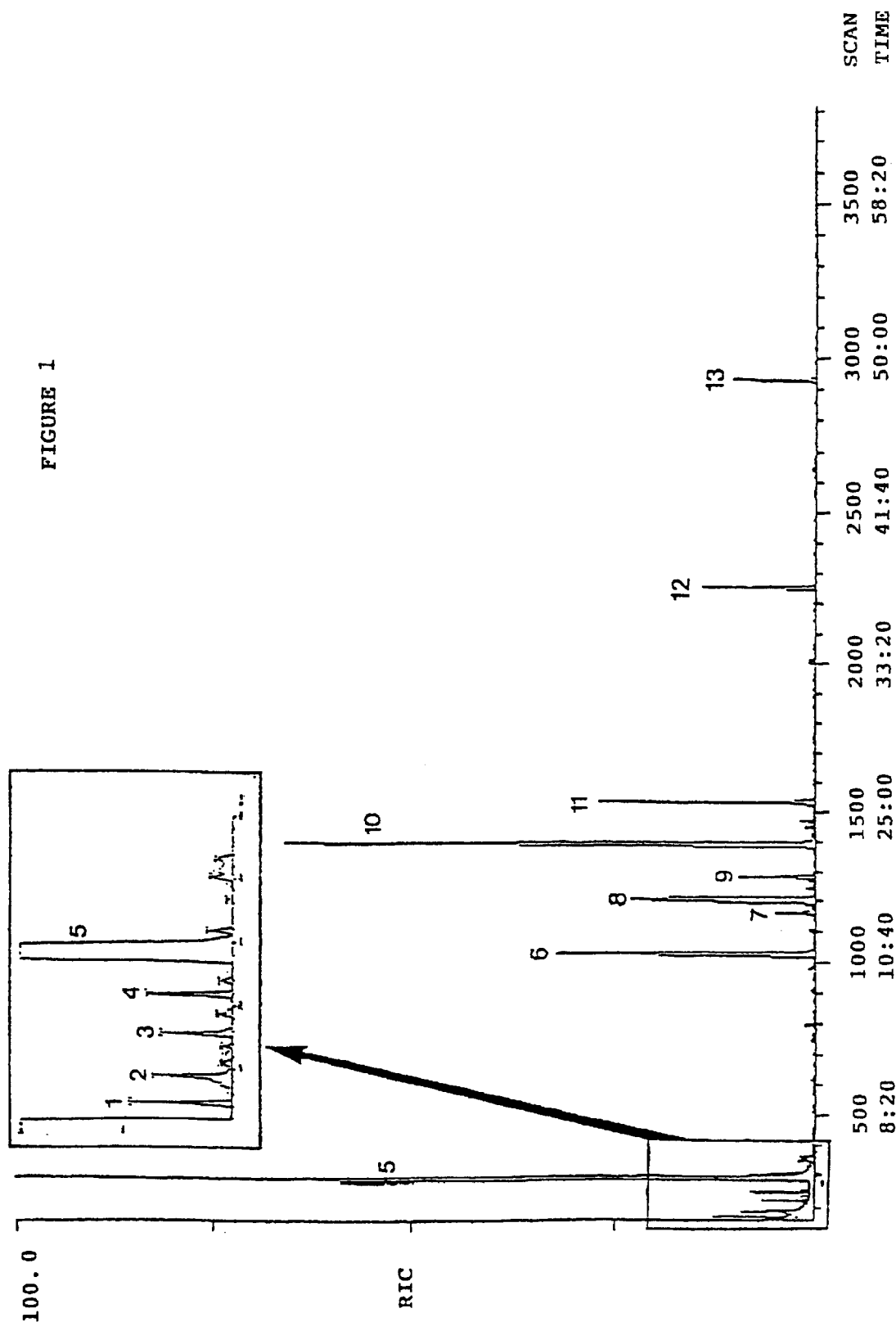

The present invention provides new formulations useful in the prevention and therapy of hair loss, based on the combination of substances with vasokinetic, antibacterial and antiandrogenic activities. It is known from the literature and from the cosmetic practice that the hair loss is negatively influenced by a reduced periferic microcirculation in the "galea capitis", by its altered relation with the bacterial flora and by an altered local androgenic methabolism. The androgens, in particular the increased deposit of dihydrotestosterone in the hair bulb, are considered to play an important role in the pathogenesis of androgenic alopecia.

In Japanese patent JP-8310923, the essential oils obtained by steam distillation of Citrus aurantium peels, and of Salvia officinalis, *Mentha piperita, Eucaliptus globulus, Artemisia princeps* and *Rosmarinus officinalis* leaves and flowers, are considered inhibitors of testosterone 5-alpha-reductase and therefore useful in the treatment of alopecia, hirsutism and seborrhoea. European patent EP-433131A claims essential oils incorporated in lipidic material in the presence of known vasodilators like methyl nicotinate or other synthetic compounds for the prevention of hair loss or of dandruff formation, and like antiparasites. The chemical composition of these essential oils is not reported and their effects are likely mediated by other synthetic compounds present in the final formulations.

Now, a mixture of monoterpenes obtained through alcoholic extraction followed by distillation of some plants alone or in combination, has surprisingly shown vasokinetic, antibacterial and antiseborrhoic activities. The antibacterial activity which was known for the essential oils, was never associated to a marked vasokinetic activity, which was demonstrated by the control of the blood flow in cutaneous areas treated before and after the application of the mixture, using Laser Doppler technique and computer videocapillary-scopy.

The monoterpene mixture, combined with salicylic acid which is known to strongly inhibit cyclooxygenase I and II, and with saturated and unsaturated fatty acids having acyl chains from 10 to 14 carbon atoms, in particular 12 carbon atoms like lauric and myristic acids, has shown particularly useful for the treatment of hair loss in normal conditions and in androgenic alopecia. The monoterpene mixture can be obtained by mixing the single commercial monoterpenes in suitable ratios, or better by mixing roots, rhizomes, leaves, barks and seeds of some hexotic plants containing essential oils, which so far have never been used in cosmetics for the prevention or the therapy of hair loss (with the exception of rosemary oil, the cosmetic use of which is known and it is based on mechanisms different from those reported in the present invention), by steeping the same in 70% ethanol and finally by collecting the alcohol which contains the desired monoterpens through distillation at room pressure.

For example, the mixture of essential oils can be obtained by steeping in 70% aqueous ethanol similar amounts of rhizomes from *Curcuma longa, Myristica fragrans, Ferule galbaniflua, Liquidambar orientalis, Alpinia officinarum, Acorus calamus, Aloe vera, Cannarium commune, Commiphora molmol, Eugenia aromatica, Cinnamonum cassia, Curcuma zedoaria, Arnica montana, Rosmarinus officinalis* and lower amounts of oil of turpentine, the vegetal material amount being comprised between 10 and 50 g, preferably 20 g of each plant, in 1.2 l of 70% ethanol for two days with stirring at room temperature, then distilling the alcohol at room pressure and collecting from 0.7 to 0.95 l of distillate, preferably 0.850 lt; this distillate, after suitable water dilution, preferably up to 50% w/w, can be used as such, after removal of the insoluble oily residue, to inhibit hair loss or it can serve as the basis for the addition of other active ingredients. In particular the mixture obtained through distillation, combined with salicylic acid and menthol, after dilutions with 25 to 75% w/w hydroalcoholic solutions, preferably up to 50%, is steeped for a period of 3 to 60 days, preferably 30 days, and it is used after removal of insoluble oily residues.

Said hydroalcoholic mixture, which contains as the main ingredients beta-pinene, camphene, beta-myrcene, limonene, cineole (I,8-epoxy-p-menthane), camphor, linalool, bornyl acetate, isobornyl acetate, menthol, terpinen-ol, isoborneol, in ratios corresponding to the gas chromatogram of the Figure, is the first object of the invention. Said chromatogram was obtained using a HP-Innowax column (cross -linked polyethylene glycol, N. of part 19091 N-133, 30 m×0.25 mm I.D., 0.25 $\mu$m film thickness), according to the following temperature program: 60° C.×5 min, 60° C. to 250° C. at 3°/min, 250° C. for 3 min; injection with PTV (Programmed Temperature Vaporizer), from 120° C. to 250° C. The addition to the mixture of salicylic acid or the salts thereof and of fatty acids with anti androgenic activity, results in a surprising synergistic effect which reduces the hair loss improving the hair growth and strength. Therefore, a second object of the invention is represented by a formulation which contains the above described mixture in combination with salicylic acid or the salts thereof, and with saturated or unsaturated $C_{10}$–$C_{14}$ fatty acids.

According to a preferred embodiment of the invention, the mixture of essential oils is obtained by steeping 20 g of *Curcuma zedoaria* rhizomes, 20 g of *Myristica fragrans* seeds, 20 g of *Cinnamomum cassia* branch bark, 20 g of *Eugenia aromatica* flowers, 20 g of *Acorus calamus* rhizomes, 20 g of *Zingiber officinalis* rhizomes and 20 g of *Alpinia officinarum*, in 0.9 l ethanol. After one day, resin oils of *Ferula galbaniflua, Liquidambar orientalis, Aloe vera, Cannarium commune, Commiphora molmol, Arnica Montana, Rosmarinus officinalis* and turpentine oil are added to the steeped product in amounts variable from 5 to 50 g, to favour the alcohol dispersion of the resin oils.

Afterwards water is added up to an alcoholic grade of about 70% and after stirring the mixture for two hours at 40° C., the distillation is started and about 0.85 l of alcoholic distillate are collected. The distillate is a colourless clear liquid with a strongly aromatic smell.

The distillate, without the addition of other substances, has vasokinetic, antibacterial and antiseborrhoic activities.

The monoterpene-containing hydroalcoholic mixture increases the volume and flow-rate at the capillary level, which, as mentioned above, is extremely important in the primitive and secondary alopecia. In fact, when the mixture is applied on the cutis, it integrates the blood flow in various organic districts and in particular it increases the blood flow in the "galea capitis" as it results from the data reported in table I, wherein the flow increment has been tested using Laser Doppler.

TABLE I

| Cutaneous blood flow variations determined using Laser Doppler after single administration of the alcoholic distillate 1:1 diluted with water. | | | | | |
|---|---|---|---|---|---|
| Substances | 0 | 30' | 60' | 90' | 120' |
| Distillate | 4.45 | 13.33 | 14.12 | 9.7 | 10.32 |
| Placebo | 5.24 | 5.63 | 7.78 | 4.64 | 6.61 |

The administration of the formulations of the invention for periods variable from one week to three months causes in humans a remarkable reduction of androgenic alopecia as it results from the data reported in tables II and III. Table II reports the flow increase caused by the application of the formulation of the example I, as evidenced by Laser Doppler analysis. Laser Doppler flowmetry was performed to test the vasokinetic effects, using the PeriFlux(R) PF3 flowmeter which is an instrument emitting a subtle bundle of 632 nm wavelenght monocromatic light, which is produced by a low potency He—Ne laser source. By this technique, the scalp blood flow was measured in basal conditions and after the application of the test products, with an interval of 15 min from the first application (acute effect) and after 30, 60 and 90 day treatment (chronic effect). The results are reported in table II.

TABLE II

Mean blood capillary flow effects induced by the topical application (90 days) of the lotion prepared according to the example I.

| | Capillary flow (AU30 m ± e.s.) | | | | |
|---|---|---|---|---|---|
| Treatment | Basal | 15 min | 30 days | 60 days | 90 days |
| Alcoholic distillate | 9.2 ± 1.0 | 23.1 ± 3.0* | 11.7 ± 2.4 | 16.8 ± 1.2* | 16.7 ± 1.1* |
| Placebo | 9.4 ± 1.2 | 10.0 ± 1.3 | 10.7 ± 1.5 | 11.0 ± 1.1 | 11.5 ± 0.9 |
| Comp. lotion | 9.3 ± 1.1 | 24.0 ± 3.1* | 18.1 ± 2.5 | 20.1 ± 1.3* | 19.4 ± 1.0* |

*= $p < 0.01$ vs basal as the result of the variance analysis of a split-plot graphic (Bonferroni's t). N = 10.

The trichograms of tested subjects randomly divided into 10 groups, were performed in order to evaluate the effect of the formulations on the hair loss inhibition at the beginning and at the end (90 days) of the treatment. The trichogram consists in the withdrawal of a suitable number (about 50) of hairs using rubberized forceps, from the superior-frontal and latero-nuchal areas.

The microscopic examination of hair roots allows to evaluate the hair quantity which is in the anagen (growth), catagen (mature) and telogen (rest) phase. The reduction in the anagen percentage and the increase in the telogen percentage, with respect to normal values (which are about 85–90% and 10–15%, respectively), represent the clinical evidence of a pathological hair loss.

TABLE III

Trichogrammic effects induced by the topical application (90 days) of the lotion prepared according to the example I

| | | Trichogram (% – m ± e.s.) | |
|---|---|---|---|
| Treatment | | telogen | anagen + catagen |
| Alc. dist. | Before | 76 ± 3 | 24 ± 1 |
| | After 90 days | 81 ± 3 | 19 ± 1 |
| Alc. dist. + Salic. Ac. | Before | 78 ± 2 | 22 ± 1 |
| | After 90 days | 82 ± 2 | 18 ± 1 |
| Ac. + dist. Ac. salic. + Fats | Before | 74 ± 2 | 26 ± 2 |
| | After 90 days | 86 ± 3* | 14 ± 1* |

*= $p < 0.01$ vs basal as the result of the calculation.

As it comes out from the data reported above, the alcoholic distillate topically applied for long periods, by the dayly administration of the preparation, exerts time-persisting favourable microvasculokinetic effects on the cutis. The trichological pharameters, telogen, anagen and catogen, behave in a similar manner. The combination of the distillate with other substances like the low molecular weight saturated and unsaturated fatty acids, which interfere with androgen receptors, leads to a clear improvement of the telogen-anagen-catagen ratios. The skin treatment through an increased blood flow and the consequent increase of nutritive substances, after few days results in a clear cutaneous modification with the increase of the number of perfused capillaries and with dandruff absence; the hair bulbs are normal and patent, with a normal sebaceous production.

The cosmetic formulations of the invention are in the form of hydroalcoholic lotions (which are preferred for the treatment of the scalp) or in the form of gels, and are used in the treatment of hair loss and seborrhoea.

The combinations which are preferred for the treatment comprise the hydroalcoholic mixture in a concentration between 5 and 20%, preferably 10%, the fatty acids between 0.1 and 0.5%, preferably 0.25%, and the salicylic acid between 0.1 and 1%, preferably 0.3%.

The treatment with these substances ranges from few days to six months. Examples of formulations according to the invention are hereafter illustrated but in any case they are not intended to limit the invention.

EXAMPLE I

Preparation of the distillate having high content of essential oils, which can be used as the basis of cosmetic formulations for the treatment of the scalp.

0.9 l of ethanol are poured in a 2 l beaker and 20 g of *Curcuma zedoaria* rhizomes, 20 g of *Myristica fragrans* seeds, 20 g of *Cinnamonum cassia* branch barks, 20 g of *Eugenia aromatica* flowers, 20 g of *Acorus calamus* rhizomes, 20 g of *Zingiber officinalis* rhizomes and 20 g of *Alpinia officinarum* are added (finely minced) with stirring and steeped for 1 day. 10 g of *Ferula falbaniflua, Liquidambar orientalis, Cannarium commune, Commiphora molmol, Rosmarinus officinalis* resin oils are added to the steeped product without removal of the vegetal material; further, 20 g of oil of turpentine are added to favour the alcohol dispersion of therein oils. After two day steeping, water is added up to an alcoholic grade of about 70% and after stirring the mixture for 2 hours at 40° C., the distillation at room pressure is started and 0.85 l of alcoholic distillate are collected. The distillate contains as the main constituents beta-pinene, comphene, beta-myrcene, limonene, cineole (1,8-epoxy-p-menthane), camphor, linalool, bornyl acetate, isobornyl acetate, menthol, terpinen-ol, isoborneol, according to the gas chromatogram reported in the Figure, the indicated ratios.

EXAMPLE II

Lotion containing essential oils, salicylic acid, lauric acid.

100 g of the lotion contain:

21 g distillate according to the example 1
0.3 g salicylic acid
0.2 g lauric acid
6.9 g rosemary essential oil
0.79 g Pantasol P
1.18 g Menthol
34 g Rhum aromatized alcohol
Demineralized water q.s. to 100 g

EXAMPLE III

Lotion containing essential oils, lauric acid, 80:20 mixture of tetrameric cyclosiloxane and pentameric cyclosiloxane.

100 g of the lotion contain:

21 g essential oil distillate according to the example I
0.2 g lauric acid
0.08 g camphor
15 g 80:20 mixture of tetrameric and pentameric cyclosiloxane
1.18 g menthol

What is claimed is:

1. Hydroalcoholic mixture of beta-pinene, camphene, beta-myrcene, limonene, cineole (1,8-epoxy-p -methane), camphor, linalol, bornyl acetate, isobornyl acetate, menthol, terpinen-ol, isoborneol monoterpens, having a chromatogram as shown in the Figure.

2. Combination of the mixture of claim 1 with salicylic acid or the salts thereof and with $C_{10}$–$C_{14}$ saturated or unsaturated fatty acids.

3. Combination according to claim 2, wherein the mixture is present in a concentration comprised between 5 and 20% w/w, the salicylic acid between 0.1 and 1%, the fatty acids between 0.1 and 0.5%.

4. Combination according to claim 3, wherein said mixture is present in a concentration of 10%, the salicylic acid in a concentration of 0.3%, the fatty acids in a concentration of 0.25%.

5. Cosmetic formulations containing the combination of claim 2 in admixture with carriers and excipients pharmaceutically acceptable.

6. Formulations according to claim 5 in the form of hydroalcoholic lotions and gels.

7. Process for the preparation of the mixture of claim 1, which comprises the steps of:

a) steeping in 70% ethanol one or more parts selected from the group consisting of roots, rhizomes, leaves, bark and seeds from *Curcuma zedoaria, Myristica fragrans, Cinnamonum cassia, Eugenia aromatics, Acorus calamus, Zingiber officinalis, Alpinia officinarum, Ferula galbaniflua, Liquidambar orientalis, Aloe vera, Cannarium commune, Commiphora molmol, Arnica montana, Rosmarinus officinalis*, together with turpentine oil, for two days with stirring at room temperature;

b) distilling the product of step a) at 40° C. at room pressure; and c) diluting the distillate of step b) with water and removing the insoluble oleous residue.

8. Process according to claim 7 wherein the plants or the parts thereof are used in amounts comprised between 10 and 50 g for each plant.

9. Process according to claim 8, wherein the amount is 20 g.

10. Hydroalcoholic mixture obtainable by the process of claim 7.

11. A method for the treatment of hair loss and of seborrhoea comprising applying to a human scalp a cosmetic formulation prepared from the hydroalcoholic mixture of claim 1, as such or in combination with salicylic acid or the salts thereof and with $C_{10}$–$C_{14}$ saturated or unsaturated fatty acids.

12. Cosmetic formulations containing the combination of claim 3 in admixture with carriers and excipients pharmaceutically acceptable.

13. Cosmetic formulations containing the combination of claim 4 in admixture with carriers and excipients pharmaceutically acceptable.

14. Formulations according to claim 12, in the form of hydroalcoholic lotions and gels.

15. Formulations according to claim 13, in the form of hydroalcoholic lotions and gels.

* * * * *